(12) United States Patent
Regensburger

(10) Patent No.: US 12,257,002 B2
(45) Date of Patent: Mar. 25, 2025

(54) METHOD FOR CREATION OF A CONTROL SIGNAL

(71) Applicant: Siemens Healthcare GmbH, Erlangen (DE)

(72) Inventor: Alois Regensburger, Poxdorf (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 685 days.

(21) Appl. No.: 17/232,256

(22) Filed: Apr. 16, 2021

(65) Prior Publication Data

US 2021/0330397 A1 Oct. 28, 2021

(30) Foreign Application Priority Data

Apr. 22, 2020 (DE) ..................... 10 2020 205 091.0

(51) Int. Cl.
*A61B 34/20* (2016.01)
*A61B 34/00* (2016.01)
*A61B 34/10* (2016.01)

(52) U.S. Cl.
CPC .............. *A61B 34/20* (2016.02); *A61B 34/10* (2016.02); *A61B 34/25* (2016.02); *A61B 2034/107* (2016.02); *A61B 2034/2055* (2016.02); *A61B 2034/2065* (2016.02); *A61B 2034/254* (2016.02)

(58) Field of Classification Search
CPC .......... A61B 34/20; A61B 34/10; A61B 34/25
See application file for complete search history.

(56) References Cited

U.S. PATENT DOCUMENTS 4,360,028 A * 11/1982 Barbier .................. A61B 6/501 378/162
4,465,069 A * 8/1984 Barbier .................. A61B 6/501 600/436

(Continued)

FOREIGN PATENT DOCUMENTS

CN 1533745 A 10/2004
CN 102089032 A 6/2011

(Continued)

OTHER PUBLICATIONS

German Office Action for German Application No. 10 2020 205 091.0 dated Feb. 12, 2021.

*Primary Examiner* — David Bilodeau
(74) *Attorney, Agent, or Firm* — Harness, Dickey & Pierce, P.L.C.

(57) ABSTRACT

A computer-implemented method is for creation of a control signal with regard to controlling a movement of a medical object, the creation of the control signal being dependent on a current movement state of an examination object. In an embodiment, the method includes receiving, via a processor, a movement model of at least one part of the examination object, the movement model including at least one target movement state; detecting, via a sensor, a current movement state of the examination object; comparing, via the processor, whether the current movement state at least approximately corresponds to the at least one target movement state; determining, via the processor, the control signal as a function of the movement model and of the current movement state, depending on a result of the comparing; and provisioning the control signal.

20 Claims, 7 Drawing Sheets

(56) References Cited

U.S. PATENT DOCUMENTS

| | | | |
|---|---|---|---|
| 4,665,914 A * | 5/1987 | Tanne | A61B 5/0538 606/166 |
| 10,039,473 B2 * | 8/2018 | Zhao | A61B 5/065 |
| 2001/0031919 A1 | 10/2001 | Strommer et al. | |
| 2004/0254680 A1 | 12/2004 | Sunaoshi | |
| 2008/0212737 A1 * | 9/2008 | D'Souza | A61N 5/1049 378/65 |
| 2010/0010382 A1 | 1/2010 | Panken | |
| 2010/0010584 A1 | 1/2010 | Skelton | |
| 2010/0114289 A1 * | 5/2010 | Camus | A61F 2/95 623/1.11 |
| 2011/0158488 A1 | 6/2011 | Cohen et al. | |
| 2013/0077756 A1 | 3/2013 | Saar | |
| 2014/0073904 A1 | 3/2014 | Biber | |
| 2015/0131780 A1 | 5/2015 | Tsunoo | |
| 2015/0196368 A1 | 7/2015 | Ecabert et al. | |
| 2016/0022166 A1 | 1/2016 | Stadler | |
| 2016/0239963 A1 | 8/2016 | Kariv et al. | |
| 2017/0084027 A1 | 3/2017 | Mintz et al. | |
| 2018/0055576 A1 | 3/2018 | Koyrakh et al. | |
| 2018/0116518 A1 | 5/2018 | Rinck | |
| 2018/0317753 A1 | 11/2018 | Hou et al. | |
| 2019/0038268 A1 | 2/2019 | Kopp | |
| 2019/0046275 A1 | 2/2019 | Winneberger | |
| 2019/0117317 A1 | 4/2019 | Abayazid et al. | |
| 2019/0246882 A1 * | 8/2019 | Graetzel | A61B 1/267 |
| 2019/0307362 A1 | 10/2019 | Piron et al. | |
| 2020/0078097 A1 | 3/2020 | Gregerson | |
| 2020/0187889 A1 | 6/2020 | Martius | |
| 2020/0297442 A1 | 9/2020 | Adebar et al. | |
| 2021/0259783 A1 * | 8/2021 | Gadda | A61B 5/066 |

FOREIGN PATENT DOCUMENTS

| | | |
|---|---|---|
| CN | 103006324 A | 4/2013 |
| CN | 103654784 A | 3/2014 |
| CN | 105662350 A | 6/2016 |
| CN | 107072576 A | 8/2017 |
| CN | 107205780 A | 9/2017 |
| CN | 107997762 A | 5/2018 |
| CN | 108261167 A | 7/2018 |
| CN | 108778113 A | 11/2018 |
| CN | 108882966 A | 11/2018 |
| CN | 109389620 A | 2/2019 |
| DE | 102007013624 A1 | 9/2008 |
| DE | 102014200326 A1 | 7/2015 |
| DE | 102018221960 B3 | 3/2020 |
| WO | WO 2017040821 A1 | 3/2017 |
| WO | WO 2017211087 A1 | 12/2017 |
| WO | WO 2018125917 A1 | 7/2018 |
| WO | WO 2019036456 A3 | 3/2019 |
| WO | WO 2019173237 A1 | 9/2019 |

* cited by examiner

METHOD FOR CREATION OF A CONTROL SIGNAL

PRIORITY STATEMENT

The present application hereby claims priority under 35 U.S.C. § 119 to German patent application number DE 102020205091.0 filed Apr. 22, 2020, the entire contents of which are hereby incorporated herein by reference.

FIELD

Example embodiments of the invention generally relate to a computer-implemented method for creation of a control signal with regard to controlling a movement of a medical object. Example embodiments of the invention further generally relate to a control apparatus, a detection apparatus, a display apparatus, a computer program product and a computer-readable storage medium.

BACKGROUND

Nowadays interventional medical procedures with a catheter are part of standard methods in medicine. In a catheter intervention or a medical intervention with a catheter the catheter is typically guided in a vascular system of a patient. In particular the catheter can be guided in a vascular system of an organ. The vascular system can deform through a movement of the patient and/or through a breathing movement of the patient and/or through a heart movement of the patient etc. Typically, in particular with periodic movements, such as for example breathing and/or a heartbeat, a catheter advance is advantageous in specific movement states. For example, with specific movement states the catheter can be guided or pushed more easily into a desired branch of the vascular system. A guidance or movement of the catheter is typically carried out either by a medical professional or by a robot.

Such an intervention is for example a transarterial chemoembolization (TACE), an endoscopic retrograde colangiopancreaticography (ERCP) or a catheter navigation in a deformable organ with a finely-branched complex vascular system. Moreover such an intervention can also be a colonoscopy or an intubation.

Nowadays complex catheter interventions, in which the catheter is guided through a branched, moving vascular system, are carried out by very skilled medical professionals. Such medical professionals are rare, which is why patients must frequently take into consideration long waiting times for complex catheter interventions or why complex procedures cannot be carried out, despite being necessary.

SUMMARY

At least one embodiment of the present invention provides a method that makes it possible to output a control signal as a function of the movement state of an examination object.

Embodiments are directed to a method for creation of a control signal with regard to controlling a movement of a medical object; an apparatus for creation of a control signal with regard to controlling a movement of a medical object; a computer program product and a computer-readable storage medium. Advantageous developments are given in the claims and in the description below.

The inventive way in which the embodiments achieved is described below both with regard to the apparatus and with regard to the method. Features, advantages or alternative forms of embodiment mentioned here are likewise to be transferred to the other subject matter and vice versa. In other words the physical claims (which are directed to an apparatus for example) can also be further developed with the features that are described or claimed in conjunction with a method. The corresponding functional features of the method are embodied in this case by corresponding physical modules.

At least one embodiment of the invention relates to a computer-implemented method for creation of a control signal with regard to controlling a movement of a medical object, wherein the creation of the control signal is dependent on a current movement state of an examination object. In this process, the method has a method step of a receipt of a movement model of at least one part of the examination object by a processor, wherein the movement model comprises at least one target movement state. A further method step is detection of the current movement state of the examination object with a sensor. A further method step is a comparison by the processor of whether the current movement state at least partly corresponds to the target movement state. In a further method step the method features a determination by the processor of the control signal as a function of the movement model and the current movement state depending on the comparison. A further method step is a provision of the control signal.

At least one embodiment of the invention moreover relates to a control apparatus for creation of a control signal with regard to controlling a movement of a medical object. In this case the creation of the control signal is dependent on a current movement state of an object. In this case the control apparatus is embodied to carry out the method described above. The control apparatus comprises a processor which is embodied to receive a movement model of at least one part of the examination object. In this case the movement model comprises at least one target movement state. The processor is moreover embodied to compare whether the current movement state at least approximately corresponds to the target movement state. The processor is moreover embodied to determine the control signal as a function of the movement model and of the current movement state. The processor is moreover embodied to provide the control signal.

At least one embodiment of the invention moreover relates to a control apparatus for creation of a control signal with regard to controlling a movement of a medical object. In this case the creation of the control signal is dependent on a current movement state of an object. In this case the control apparatus is embodied to carry out the method described above. The control apparatus comprises a processor which is embodied to receive a first medical image dataset. In this case the first medical image dataset represents the at least one part of the examination object. The processor is moreover embodied to determine a movement model of the at least one part of the examination object. In this case the movement model is determined based on the first medical image dataset. The processor is moreover embodied to compare whether the current movement state at least approximately corresponds to the target movement state. The processor is moreover embodied to determine the control signal as a function of the movement model and of the current movement state. The processor is moreover embodied to provide the control signal.

At least one embodiment of the invention also relates to a detection apparatus which is connected to the control apparatus for transmission of information with regard to a current movement state. The detection apparatus comprises a sensor which is embodied to detect the current movement state.

At least one embodiment of the invention also relates to a display apparatus for output of the control signal.

At least one embodiment of the invention also relates to a computer program product with a computer program as well as to a computer-readable medium. A largely software-based realization has the advantage that the control apparatus already used can easily be upgraded by a software update in order to work in the way described. Such a computer program product, as well as the computer program, can if necessary comprise further elements such as e.g. documentation and/or additional components, as well as hardware components, such as e.g. hardware keys (dongles etc.) for use of the software.

In particular, at least one embodiment of the invention also relates to a computer program product with a computer program, which is able to be loaded directly into a memory of a control apparatus, with program sections for carrying out all steps of the method of at least one embodiment, for creating a control signal for controlling a movement of a medical object described above when the program sections are executed by the control apparatus.

In particular, at least one embodiment of the invention relates to a computer-readable storage medium, on which program sections able to be read and executed by a determination system and/or a training system are stored, in order to carry out all steps of at least one embodiment of the method described above for creation of a control signal for controlling a movement of a medical object when the program sections are executed by the control apparatus.

In particular, at least one embodiment of the invention also relates to a computer-implemented method for creation of a control signal with regard to controlling a movement of a medical object, the creation of the control signal being dependent on a current movement state of an examination object, the computer-implemented method comprising:

receiving, via a processor, a movement model of at least one part of the examination object, the movement model including at least one target movement state;

detecting, via a sensor, the current movement state of the examination object;

comparing, via the processor, whether the current movement state at least approximately corresponds to the at least one target movement state;

determining, via the processor, the control signal as a function of the movement model and of the current movement state, depending on a result of the comparing; and provisioning the control signal.

In particular, at least one embodiment of the invention also relates to a computer-implemented method for creation of a control signal with regard to controlling a movement of a medical object, the creation of the control signal being dependent on a current movement state of an examination object, the computer-implemented method comprising:

receiving, via a processor, a first medical image dataset, the first medical image dataset representing at least one part of the examination object;

determining, via the processor, a movement model of the at least one part of the examination object based on the first medical image dataset, the movement model including at least one target movement state;

detecting, via a sensor, a current movement state of the examination object;

comparing, via the processor, whether the current movement state at least approximately corresponds to the at least one target movement state;

determining, via the processor, the control signal as a function of the movement model and of the current movement state, depending on a result of the comparing; and provisioning the control signal.

In particular, at least one embodiment of the invention also relates to a control apparatus for creation of a control signal, with regard to controlling a movement of a medical object, dependent on a current movement state of an examination object, the control apparatus comprising:

a processor, embodied to receive a movement model of at least one part of the examination object, the movement model including at least one target movement state, the processor being further embodied to compare whether the current movement state at least approximately corresponds to the target movement state;

determine the control signal as a function of the movement model and of the current movement state; and provide the control signal.

In particular, at least one embodiment of the invention also relates to a detection apparatus, connected to the control apparatus of an embodiment, for transmission of information with regard to a current movement state, comprising:

a sensor, embodied to detect the current movement state.

In particular, at least one embodiment of the invention also relates to a display apparatus, for output of the control signal of the control apparatus of an embodiment.

In particular, at least one embodiment of the invention also relates to a non-transitory computer program product storing a computer program, loadable into a memory of control apparatus, including program sections for carrying out the method of an embodiment when the program sections are executed by the control apparatus.

In particular, at least one embodiment of the invention also relates to a non-transitory computer-readable storage medium, storing readable and executable program sections, to carry out the method of an embodiment when the program sections are executed by a control apparatus.

BRIEF DESCRIPTION OF THE DRAWINGS

The characteristics, features and advantages described above will be become clearer and easier to understand in conjunction with the figures below and their descriptions. In this case the figures and descriptions are not intended to restrict the invention and its forms of embodiment in any way. In different figures the same components are labeled with corresponding reference characters. The figures are as a rule not true-to-scale.

In the figures

DETAILED DESCRIPTION OF THE EXAMPLE EMBODIMENTS

Figure 1:
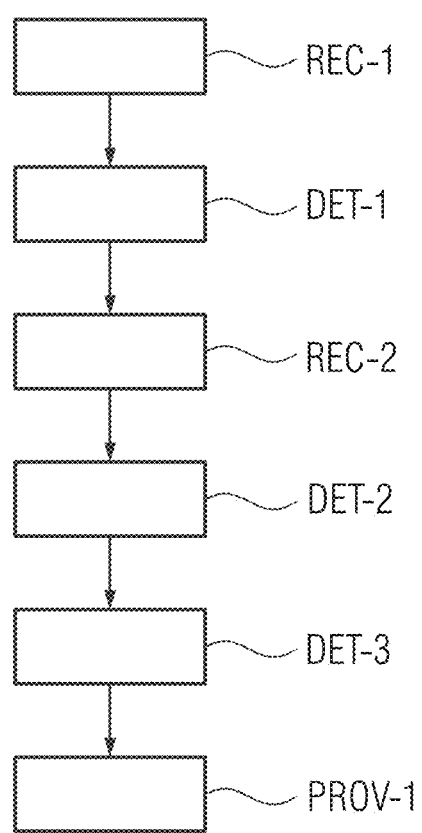
FIG. 1 shows a flow diagram of a first example of an example embodiment of the method for creation of a control signal for controlling a movement of a medical object.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a computer-implemented method for creation of a control signal with regard to controlling a movement of a medical object, wherein the creation of the control signal is dependent on a current movement state of an examination object. In this process, the method has a method step of a receipt of a movement model of at least one part of the examination object by a processor, wherein the movement model comprises at least one target movement state. A further method step is detection of the current movement state of the examination object with a sensor. A further method step is a comparison by the processor of whether the current movement state at least partly corresponds to the target movement state. In a further method step the method features a determination by the processor of the control signal as a function of the movement model and the current movement state depending on the comparison. A further method step is a provision of the control signal.

In particular the medical object can be embodied for example as a surgical instrument and/or diagnostic instrument. In particular the medical object can be elongated and/or flexible. The medical object can be embodied for example as a catheter and/or endoscope and/or guide wire.

In particular the movement of the medical object can comprise a rotation and/or a forwards movement and/or a backwards movement and/or a flexing of the medical object. In particular the control signal can describe the movement that the medical object is to carry out. In particular the movement can comprise a movement from a current position to a target position.

In particular the examination object can be a human or an animal. As an alternative the examination object can be a human dummy. In particular the human dummy can simulate movements of a human being. In particular the human dummy can simulate movements in a vascular system of a human being. The vascular system comprises vascular sections or sections and vascular branches or branches. The vascular system can in particular be filled partly or completely with a gas, with a fluid (e.g. blood, bile, water, urine) and/or with digestive tract content. The vascular system can in particular be encompassed by an organ. The organ can for example be a liver or a pancreas or a heart or a brain etc. of the examination object. In particular the vascular system can have branches that deform with the movement and/or the position or positioning or support of the examination object. In particular a movement of the examination object can for example be a breathing movement and/or a heart movement and/or a movement of the digestive system. In particular the deformation of the vascular system can be accompanied/caused/predetermined/influenced by a deformation of a surrounding/enclosing organ.

The current movement state of the examination object is the movement state in which the examination object finds itself at a current point in time. The current movement state can depend on the position or support of the examination object. As an alternative or in addition the current movement state can for example depend on a breathing cycle and/or a heart cycle of the examination object at the current point in time.

The movement model comprises at least one possible movement state of the examination object. In particular the movement model comprises a variable that describes the at least one movement state. In particular the variable can be a medical image, an electrical signal, an optical image etc. In particular the movement state can be described for example by a medical image and/or by an electrocardiogram signal and/or by an image recording and/or by a signal of a motion sensor.

In particular the movement model advantageously comprises the movement state of the examination object during which the movement of the medical object can best be carried out. In particular this movement state is referred to as the target movement state. In particular the target movement state can be different for different positions in the vascular system. In particular the movement model then comprises the corresponding target movement state at least for the corresponding position in the vascular system. In particular the movement model can comprise a multiplicity of possible movement states of the examination object. In this case at least one of the movement states is the target movement state. In particular the target movement state can also be a chronological sequence of movement states.

In particular it is known from the movement model how vascular branches and/or vascular sections of the vascular system are formed within the at least one part of the examination object for different movement states. In particular the form of the vascular system of the at least one part of the examination object is known for the target movement state on the basis of the movement model. In particular the target movement state can be determined based on the movement model.

The current movement state of the examination object is detected via the sensor. In particular this is done in the method step of detection of the current movement state of the examination object. In particular the sensor can be embodied as an image sensor and/or a motion sensor and/or an electrical sensor etc. In particular the current movement state of the examination object can be detected continuously via the sensor. As an alternative the sensor can detect simulated movement states of the human dummy.

In particular, at any point in time, the current movement state that is detected by the sensor can be reconciled with the target movement state. This is done in particular in the method step of comparing whether the current movement state at least approximately corresponds to the target movement state. At least approximately means that the current movement state and the target movement state match or that the current movement state and the target movement are similar with a maximum deviation. The maximum deviation in this case can be predetermined. In particular the reconciliation can take place as a function of the sensor by way of image registration and/or template matching and/or evaluation of a signal value of the sensor etc. In particular the sensor detects a sensor signal. In particular the reconciliation can be carried out based on a comparison sensor signal. The comparison sensor signal can have been detected during the target movement state. As an alternative the comparison sensor signal can be determined or interpolated for the target movement state. In particular the comparison sensor signal is equivalent to the sensor signal. In particular the comparison sensor signal can be compared to or reconciled with the sensor signal. In particular the reconciliation enables it to be recognized when the current movement state corresponds to the target movement state.

In the method step of comparing whether the current movement state at least approximately corresponds to the target movement state it can be signaled for example with a trigger that the next method step is to be carried out. In particular the trigger can be activated when the comparison is positive, i.e. when the current movement state at least approximately corresponds to the target movement state.

The trigger signal can in particular be a data signal, which initiates the next method step.

When the current movement state at least approximately corresponds to the target movement state based on the comparison, the control signal can be determined in the method step of determination of the control signal based on the movement model. In particular the control signal specifies how and in which direction the medical object is to be moved when the current movement state of the examination object corresponds to the target movement state. In particular the control signal specifies how and in which direction the medical object must be moved so that it can be guided or moved through the vascular system to the target position. As an alternative or in addition the control signal can be a trigger signal for carrying out the movement of the medical object. In particular the trigger signal can be optical, acoustic, electrical and/or digital. In particular the trigger signal can initiate the movement of the medical object. In particular the control signal can specify when the movement of the medical object is to be carried out. In particular the control signal is determined for the target movement state in the movement model. In particular the control signal can have been determined for a number of movement states in the movement model. In particular the control signal can have been determined for each movement state in the movement model. In this case, in the method step of determination of the control signal, the control signal that describes the movement of the medical object for the target movement state is "sought out".

In the method step of provision of the control signal the control signal is provided for the movement of the medical object.

The inventors have recognized that the provision of a control signal as a function of the current movement state of the examination object makes it possible for even an inexperienced medical professional and/or a robot to control the movement of the medical object in the vascular system. Moreover the inventors have recognized that the state can be defined, based on the movement model, in which the medical object can be guided most easily and/or with maximum tissue protection in the desired branch of the vascular system. In particular the inventors have recognized that this target state can be displayed by way of the control signal.

Moreover the inventors have recognized that the control signal can serve as assistance to the medical professional. The inventors have recognized that, in particular when the examination object assumes the target movement state for just a very short time, for example a fraction of a second, the control signal can support and/or guarantee an exactly timed coordinated movement of the medical object.

According to a further embodiment of the invention the method, as an alternative to the method step of receipt of the movement model, comprises a method step of receipt of a first medical image dataset by a processor, wherein the first medical image dataset represents the at least one part of the examination object. The method then moreover comprises a method step of determination of the movement model of the at least one part of the examination object with the processor, wherein the movement model is determined based on the first medical image dataset.

In particular the two method steps of receipt of the first medical image dataset and of determination of the movement model are carried out as an alternative to the method step of receipt of the movement model.

The first medical image dataset can be acquired by way of a medical imaging apparatus and received by the processor. The first medical image dataset can in particular be a four-dimensional Computed Tomography (CT) image dataset. The four-dimensional CT image dataset comprises a multiplicity of medical images that were recorded at different points in time. In particular the four-dimensional CT image dataset can comprise images of at least one part of the examination object over a complete breathing cycle and/or over a complete heart cycle. As an alternative the first medical image dataset can be an individual CT dataset and/or a Dyna-CT dataset and/or a magnetic resonance tomography dataset and/or a three-dimensional ultrasound dataset and/or a concatenation of two-dimensional and three-dimensional datasets. In other words the first medical image dataset can comprise an individual medical image. In particular each medical image encompassed by the first medical image dataset can represent a movement state of the examination object.

In particular at least one part of the examination object is shown in the first medical image dataset. In particular the part of the examination object comprises at least the vascular system. In particular the organ, in the vascular system of which the medical object is to be moved by way of the control signal, can be shown in the first medical image dataset.

The movement model is determined in the method step of determination of the movement model for the at least one part of the examination object. The movement model is determined based on the first medical image dataset. The movement model comprises at least one possible movement state of the examination object. In particular the movement model comprises at least the movement states of the examination object that are shown in the first medical image dataset. In particular the movement model can comprise the at least one movement state in the form of a medical image or in the form of a modeled medical image. The modeling of such an image will be explained below.

When the formulation "the movement model comprises the movement state" is used below, this means that the movement model comprises the medical image that at least approximately represents the movement state or a modeled medical image that at least approximately represents the movement state or an abstracted representation of the possibly modeled movement state. The abstracted representation can for example comprise a representation of just a center line of the vascular system. The center line can describe the course of the vascular system. Alternative abstraction approaches are possible.

In particular the movement model comprises at least the movement state or the movement states that are detected in the first medical image dataset.

In particular the movement model can comprise movement states that are determined based on the first medical image dataset by way of biomechanical modeling. In other words the movement model can be determined by biomechanical modeling. For biomechanical modeling material properties of the at least one part of the examination object are known and/or derived from typical values. Such material properties can for example be a rigidity, a surface structure, a deformability, etc. By way of the material properties the movement of the at least one part of the examination object can be modeled. In particular, based on at least one medical image, which is encompassed by the first medical image dataset, the movement of the at least one part of the examination object is modeled for different positions or supports and/or a breathing cycle and/or a heart cycle. When the first medical image dataset comprises a chronological sequence of medical images, movement states between the individual medical images can be modeled by way of biomechanical modeling. In other words the movement of the at least one part of the examination object can be interpolated between the medical images of the first medical image dataset. In particular the target movement state of the examination object can be modeled in this way if it is not encompassed by the first medical image dataset.

In particular it is thus known from the movement model how vascular branches and/or vascular sections of the vascular system within the at least one part of the examination object are formed for different movement states. In particular the form of the vascular system of the at least one part of the examination object is known for the target movement state on the basis of the movement model. In particular the target movement state can be determined based on the movement model.

The inventors have recognized that, based on a medical image dataset, a movement model can be determined. Moreover the inventors have recognized that movement states in the movement model can be determined by way of biomechanical modeling. Moreover the inventors have recognized that a target movement state can be determined based on the movement model.

According to a further embodiment of the invention at least the one target movement state of the movement model is linked to a comparison sensor signal.

In particular the movement model can comprise more than one movement state. In particular each of the movement states of the movement model can then be linked to a comparison sensor signal. In particular a movement state then corresponds to a comparison sensor signal.

In particular a sensor for determination of the comparison sensor signal can be a motion sensor, an electrical sensor, an optical sensor etc. In particular the comparison sensor signal can be a breathing state, a signal of an electrocardiogram (EKG), a support state or positing state and/or a further image dataset of the examination object. In particular the comparison sensor signal can have been detected at the same point in time at which the corresponding movement state of the movement model was detected. In particular the corresponding movement state represented in this way in the first medical image dataset can be linked or correlated with the variable detected by the sensor.

In particular the first medical image dataset can be linked to a comparison sensor signal. In particular the comparison sensor signal can be detected during a recording of the first medical image dataset and linked in terms of time to the first medical image dataset. In particular a number of movement states of the medical image dataset can be linked to a comparison sensor signal. In particular each movement state of the medical image dataset can be linked to a comparison sensor signal. In particular the comparison sensor signal can likewise be modeled during the biomechanical modeling for determination of the movement model in a similar way to the movement states. In particular the comparison sensor signal can be encompassed by the movement model. The comparison sensor signal can for example be an EKG signal and/or a signal dependent on the breathing cycle and/or a signal from an optical image dataset etc.

As an alternative the comparison sensor signal can be derived from the movement states of the movement model.

In particular the comparison sensor signal can be the first medical image dataset and/or the modeled movement states.

In particular the comparison sensor signal can be equivalent to the signal of the sensor that is embodied to detect the current movement state. In particular the two sensor signals can be comparable.

The inventors have recognized that the comparison of the current movement state with the target movement state is simplified if the target movement state is linked to a comparison sensor signal and the current movement state is detected with an equivalent sensor. In this way it is easily possible for example to reconcile the current breathing state or the current heart movement with the breathing state or the heart movement of the target movement state.

According to a further embodiment of the invention the method moreover comprises a method step of determination of a movement path, wherein the movement path describes a spatial direction of the movement of the medical object. In this case the determination of the movement path is based on the movement model.

In particular the determination of the movement path is carried out after the determination of the movement model. In particular the determination of the movement path is carried out before the determination of the control signal. In particular the determination of the movement path can be carried out before the detection of the current movement state. As an alternative the determination of the movement path can be carried out before the comparison as to whether the current movement state corresponds at least approximately to the target movement state. As an alternative the determination of the movement path can be carried out after the comparison as to whether the current movement state corresponds at least approximately to the target movement state.

In particular the movement path describes the path that the medical object must follow so that it can be guided from the current position to the target position.

In particular the movement path describes the spatial direction of the movement that the medical object is to carry out in the vascular system. In particular the movement path can describe a sequence of spatial directions of the movement depending on the position in the vascular system.

The spatial direction of the movement can in particular describe a forwards or a backwards movement of the medical object in the vascular system. The spatial direction of the movement can in particular comprise "forwards", "backwards", "left", "right", "up", "down" and/or the directions inbetween. Moreover the spatial direction can describe a rotation. In particular the spatial direction can describe whether the rotation is to be carried out in the clockwise or the counterclockwise direction.

In particular the determination of the movement path can be done manually and/or automatically based on the movement model. In particular the automated determination can be done by way of a segmentation of the vascular system. Moreover the automated determination can be done by way of a skeletonizing algorithm. In particular the automated determination can be undertaken by solving a minimization problem. In particular in this case the path along the skeletonized vessels from a current position in the vascular system to a target position in the vascular system can be minimized. As an alternative the movement path can be determined by way of machine learning.

In particular the determination of the movement path can be done at least for the target movement state. In particular the movement path can be determined for more than one of the movement states encompassed by the movement model. In particular the movement path can be done for all of the movement states encompassed by the movement model. In particular the movement path can be determined for a combination of a number of target movement states.

In particular the target movement state in the movement model can be determined by the determination of the movement path. In particular the target movement state can correspond to the movement state in the movement model, in which for example the movement path is minimal and/or in which the vascular sections through which the movement path runs have a greatest diameter by comparison. As an alternative or in addition the target movement state can correspond to the movement state in the movement model in which the movement path has maximum radii of curvature.

In particular the target movement state can be a chronological sequence of movement states, of which the combination optimizes the movement path according to criteria described above.

The inventors have recognized that the optimal path that the medical object is to follow to reach the target position can be described with the movement path. Moreover the inventors have recognized that the spatial direction of the movement of the medical object necessary for following the path can be derived from the movement path.

In accordance with a further embodiment of the invention the movement path for the target state is determined in the movement model.

The movement path is determined in this case as described above at least for the target movement state in the movement model. In particular the target movement state can be different for different positions in the vascular system.

The inventors have recognized that, through the determination of the movement path for the target movement state, the optimal path of the medical object from a current position to a target position can be provided. Moreover the inventors have recognized that computing time can be saved and the determination of the movement path can be speeded up if the movement path is determined only for the target movement state.

In accordance with a further embodiment of the invention, the detection of the current movement state is done in particular by detection of a breathing state and/or by detection of an EKG signal and/or by optical tracking of the examination object and/or by detection of a current image dataset.

In particular the detection of the current movement state can comprise the detection of the breathing state of the examination object. For this a breathing movement of the examination object can be detected. In particular the breathing movement can be made visible by way of optical markers and detected by a camera. In particular the optical markers can be arranged in the chest region of the examination object. In particular the sensor for detection of the current movement state comprises the camera and the optical markers. As an alternative the breathing movement can be detected and/or controlled by way of a respirator system. In particular the sensor then comprises the respirator system.

In particular the detection of the current movement state can comprise the detection of heart flows or of potentials through the heart of the examination object by way of an EKG (electrocardiogram). In particular, based on the EKG, the current movement state of the heart of the examination object can be determined. In particular the sensor then comprises the EKG device.

In particular the current movement state of the examination object can generally be detected by optical tracking. In particular optical markers can be attached to the examination object for this, the movement of which is recorded by a camera. As an alternative the movement of the examination object can be recorded without markers by a camera. In particular the sensor then comprises the camera and if necessary the markers.

In particular the current movement state of the examination object can be detected by the detection of the current image dataset. In particular the current image dataset can be acquired with a CT device or with a C-arm device or with a flat image x-ray device or with a magnetic resonance tomography device or with a 3D ultrasound device, etc. In particular the current image dataset can be acquired with a combination of these devices. In particular the devices can be coupled to one another in terms of time. In particular the current image dataset can be compared with the first medical image dataset for detection of the movement. In particular the sensor then at least comprises one image sensor for detection of the current image dataset.

In particular the current movement state of the examination object can be determined by at least one motion sensor, which is arranged on the medical object. In particular the motion sensor can be an acceleration sensor and/or a force sensor. In particular this motion sensor can detect a deformation of the medical object in the vascular system through the movement of the examination object. In particular the sensor then comprises the motion sensor.

In particular a sensor can be arranged on the medical object, which detects a bending, a shape, a spatial location of the medical object and/or a force that the medical object exerts on surrounding tissue. In particular the current movement state of the examination object can be determined from this data.

In particular the current movement state of the examination object can also be detected by way of at least one motion sensor, which is arranged on the examination object and/or on at least one organ of the examination object. In particular the motion sensor can be embodied as an acceleration sensor. In particular the sensor for detection of the movement of the current movement state then comprises the at least one motion sensor.

In particular the current movement state can be detected with a combination of the options described above. In particular the sensor can comprise such a combination. In particular the different signals from the combination can be coupled by way of temporal tracking.

In particular the current movement state, which corresponds to the format of the movement states in the movement model, can be derived from the sensor signals. In particular the derived current movement state is then comparable with the at least one movement state in the movement model.

As an alternative the sensor can detect a signal equivalent to the comparison sensor signal. In particular the signal of the sensor can then be comparable with the comparison sensor signal. In particular the sensor for detection of the comparison sensor signal can be embodied as equivalent to the sensor for detection of the sensor signal of the current movement state. In other words a sensor can be used for detection of the comparison sensor signal, which is embodied as equivalent to the sensor for detection of the current movement state. Equivalent means that both sensors detect comparable signals.

The inventors have recognized that the current movement state of the examination object can be determined by way of a selection from a plurality of sensors. Moreover the inventors have recognized that the current movement state can be derived from the sensor signals. Moreover the inventors have recognized that a comparison of the current movement state with the movement state of the movement model is made possible in this way.

According to a further embodiment of the invention, a bringing about of the target movement state is suggested in particular through a support of the examination object determined from the movement model and/or by exerting a specific force on the examination object and/or with the aid of a display apparatus and/or with the aid of specifications with regard to the breathing and/or by a respirator unit.

In other words it can be suggested how the target movement state of the examination object can be explicitly brought about. In particular the suggestion can be made by way of display apparatus to a medical professional. In particular it can be notified or suggested in writing and/or acoustically to the medical professional how the target movement state of the examination object can be brought about. In particular it can be described in writing how the target movement state can be brought about. In particular it can be shown in the form of pictograms how the target movement state can be brought about. In particular it can be described acoustically how the target movement state can be brought about. As an alternative the suggestion can be a data signal to a unit, which acts on the examination object in such a way that the target movement state is brought about.

In particular the target movement state can be brought about by a support of the examination object determined from the movement model. In other words a position can be determined from the movement model in which the examination object is in the target movement state. In particular the medical professional can support the examination object in such a way that it finds itself in the position determined from the movement model. In particular the position or support for example can be described by the examination object being located on their stomach and/or located on their back and/or located on their side. In particular through the explicit support of the examination object, the vascular system can be shaped by gravity and/or by pressure from other organs of the examination object on the vascular system in such a way that the target movement state is brought about.

As an alternative the target movement state can be brought about by the exertion of a specific force on the examination object by the medical professional. In particular the medical professional can press on regions, such as for example the stomach of the examination object. In particular in this way the organs can be deformed and/or shifted in such a way that the target movement state is brought about.

As an alternative the target movement state can be brought about with the aid of a display on a display apparatus. In particular the examination object can be shown how it should be positioning itself or moving so that the target movement state is brought about. In particular the displays can show pictograms and/or text that describe how the examination object should move and/or position itself, so that it assumes its target movement state.

As an alternative requirements with regard to breathing can be specified to the examination object so that it can assume the target movement state. In particular it can be specified to the examination object directly by a display apparatus or acoustically or indirectly via the medical professional how it is to breathe. In particular such a specification can for example be "breathe-in deeply" or "hold your breath" or "breathe out slowly" etc.

As an alternative the target movement state can be brought about by way of the respirator unit. In particular the data signal can be sent to a respirator unit. In particular the examination object can breathe with the respirator unit. In particular the respirator unit can control the breath of the examination object in such a way that the target movement state is achieved. In particular the respirator device can cause very rapid, level breathing. In particular the respirator device can cause holding of the breath in any given breathing state.

The inventors have recognized that, through the suggestion of how the target movement state can be brought about as efficiently as possible, the control signal can be provided more quickly. In particular the medical object can be moved more quickly to its target position in this way since the control signal can be provided quickly.

In accordance with a further embodiment of the invention, the control signal describes direction and orientation of a movement of the medical object and/or triggers the movement of the medical object.

In particular the control signal describes how and in which direction the medical object is to move. In other words the control signal describes the movement of the medical object. In particular the control signal can describe a movement of the medical object. As an alternative the control signal can describe a sequence of movements of the medical object.

In particular the control signal can describe the direction in which the medical object is to move or is to be moved. In particular the control signal can describe whether the movement of the medical object is to be forwards, backwards, upwards, downwards, to the right, to the left or in a direction between these directions.

In particular the control signal can describe how the movement is made in the predetermined direction. In particular the control signal can for example describe a simple linear movement or through a rotational movement about an axis of the medical object or through a bending of the axis of the medical object, etc. In particular the control signal can describe a direction and/or a radius of this bending.

As an alternative or in addition the control signal can trigger the movement of the medical object. In particular the control signal can be an optical and/or acoustic and/or electrical and/or digital etc. trigger which initiates the movement of the medical object.

The inventors have recognized that the actual movement of the medical object can be described by the control signal. The actual movement is the movement that the medical object carries out so that it can follow the movement path. The inventors have recognized that the control signal will subsequently be used for the actual movement of the medical object.

According to a further possible embodiment of the invention, the control signal describes when the target movement state at least approximately corresponds to the current movement state.

In other words the control signal describes when the target movement state is likely to be reached or assumed.

In particular, based on the sensor signals, which describe the current and preceding current movement states, it can be extrapolated as to when the current movement state corresponds to the target movement state. In particular data, which is acquired in the step of detecting the current movement state, can be analyzed for this over time. In particular, based on this analysis, a prediction can be made as to when the current movement state corresponds to the target movement state. In particular it can be derived or extrapolated from this when the movement of the medical object described by the control signal should be carried out.

In particular an extrapolation of this type can be carried out for a cyclical movement of the examination object. In particular for a cyclical breathing movement or a cyclical heart movement, it can be concluded from previous measurements of the current movement state when the current movement state corresponds to the target movement state. In particular a point in time of a likely or forecast point at which the target movement state is reached within a periodic movement cycle can be determined.

In particular an extrapolation of this type can also be carried out for non-cyclical movement sequences. In particular, based on prior sensor signals of the current movement state, it can be extrapolated on a model or formula basis when the target movement state is reached. In particular the predicted point in time of reaching the target movement state can be determined.

In particular the control signal can then be provided early. In other words the control signal can be provided before the current movement state corresponds to the target movement state. In particular the control signal can be output at a defined time interval before the predicted point in time of reaching the target movement state. In particular the control signal can specify when the target movement state occurs and when accordingly the movement of the medical object is to be carried out.

The inventors have recognized that it is advantageous when the control signal comprises information about a point in time of the occurrence of the target movement state. It is thus possible to provide the control signal already before the occurrence of the target movement state. This makes it possible for the medical professional or the robot to anticipate and prepare early for carrying out the movement of the medical object.

According to a further embodiment of the invention, the control signal is output on a display apparatus.

In particular the control signal can be provided to a display apparatus. In particular the control signal is output in such a way that a medical professional can move the medical object in accordance with the control signal output. In particular the control signal can be output in text form and/or pictorially to the display apparatus. In particular the direction and/or the type of the movement can be output in text form. For example the text "forwards", "rotate" or "left, 90° bend" can be output. As an alternative or in addition the movement can be shown in pictorial form, in particular in the form of pictograms, on the display apparatus. As an alternative the movement can be shown superimposed on a current medical image. In particular for example the movement of the medical object can be shown by way of arrows. In particular the control signal can serve as assistance for a medical professional.

In particular how long it will be before the target movement state corresponds at least approximately to the current movement state can be displayed. In particular a countdown can be displayed which shows the remaining time until the movement of the medical object is carried out.

The inventors have recognized that in this way less skilled professionals can also move or guide the medical object. Moreover the inventors have recognized that medical personnel can be trained in this way, in particular on a human dummy.

According to a further possible embodiment of the invention the control signal is forwarded as a data signal to a robot.

In particular the robot can be embodied to move or to guide the medical object. In particular the control signal specifies to the robot how and/or when it should move the medical object.

The inventors have recognized that the control signal can also serve to activate a robot.

In accordance with a further embodiment of the invention, the control signal is only provided when the medical object gets closer than a predetermined distance from a critical point. In this case the critical point is derived from the movement model.

The critical point is for example a narrow branch or a section of the vessel, which changes greatly depending on the movement state of the examination object. A critical point can be characterized by the medical object being able to be guided or moved with different degrees of difficulty in the desired vessel section or through the desired vessel branch in different movement states.

In particular the medical object can be moved easily outside the critical point. In particular a movement of the medical object outside of the critical point is lower-risk than a movement through the critical point.

In particular the critical point can be marked in the movement model. In particular the critical point can be marked manually or automatically. In particular the marking of the critical point depends for example on a vessel diameter, on a movement of the critical point as a function of the movement state and/or on a degree of branching at the location of the critical point. In particular a distance can be predetermined or predefined or specified from which, in accordance with the method, the control signal should be provided. In other words the control signal is provided when the distance is undershot. This means that the control signal is provided when the medical object is closer to the critical point than specified by the distance.

The distance can be predetermined by the medical professional. In particular the distance can be adapted by the medical professional for each intervention or be dependent on the medical professional carrying out the intervention. As an alternative a fixed value can be predetermined for the distance. As an alternative the distance can be determined in an automated manner. In particular the distance can be determined in an automated manner as a function of the critical point. In particular the distance can be determined as a function of the vessel diameter, the degree of branching and/or the movement of the critical point. The more critical the point, the greater the predetermined distance can be.

In particular the medical object, if it is at a greater distance from the critical point, can be moved freely without any control signal.

In particular more than one critical point can be determined for the vascular system. In particular the distance can be different for the critical points.

The inventors have recognized that the provision of the control signal is not necessary in each section or for each medical professional. In particular the inventors have recognized that the movement of the medical object to the target position can be speeded up when control signals are only provided at the critical points.

In accordance with a further embodiment of the invention, the method steps of detection of the current movement state of the examination object with a sensor, of comparing whether the current movement state at least approximately corresponds to the target movement state, of determination of the control signal as a function of the movement model and of the current movement state with the processor, are carried out in a loop as a function of the comparison and of the provision of the control signal.

In particular the method steps over a multiplicity of critical points can be carried out in a loop. In particular the loop can comprise at least one loop execution. In particular the loop can comprise as many executions of the loop as would move the medical object from its start position to its target position. In particular a multiplicity of control signals can be provided. In particular a control signal can be provided in a number of or in each loop execution. In particular the multiplicity of control signals can be embodied to move the medical object from a start position to the target position. In particular a control signal dependent on the current position of the medical device in the vascular system can be provided in a number of loop executions or in each loop execution.

The inventors have recognized that the method steps for provision of the control signal are advantageously carried out in a loop, so that the overall movement of the medical object from the start position to the target position can be described by control signals.

At least one embodiment of the invention moreover relates to a control apparatus for creation of a control signal with regard to controlling a movement of a medical object. In this case the creation of the control signal is dependent on a current movement state of an object. In this case the control apparatus is embodied to carry out the method described above. The control apparatus comprises a processor which is embodied to receive a movement model of at least one part of the examination object. In this case the movement model comprises at least one target movement state. The processor is moreover embodied to compare whether the current movement state at least approximately corresponds to the target movement state. The processor is moreover embodied to determine the control signal as a function of the movement model and of the current movement state. The processor is moreover embodied to provide the control signal.

Such a control apparatus can in particular be embodied to carry out an embodiment of the method described above for creation of a control signal for controlling a movement of a medical object. The control apparatus is embodied to carry out this method in that the processor is embodied to carry out the corresponding method steps.

At least one embodiment of the invention moreover relates to a control apparatus for creation of a control signal with regard to controlling a movement of a medical object. In this case the creation of the control signal is dependent on a current movement state of an object. In this case the control apparatus is embodied to carry out the method described above. The control apparatus comprises a processor which is embodied to receive a first medical image dataset. In this case the first medical image dataset represents the at least one part of the examination object. The processor is moreover embodied to determine a movement model of the at least one part of the examination object. In this case the movement model is determined based on the first medical image dataset. The processor is moreover embodied to compare whether the current movement state at least approximately corresponds to the target movement state. The processor is moreover embodied to determine the control signal as a function of the movement model and of the current movement state. The processor is moreover embodied to provide the control signal.

At least one embodiment of the invention also relates to a detection apparatus which is connected to the control apparatus for transmission of information with regard to a current movement state. The detection apparatus comprises a sensor which is embodied to detect the current movement state.

In particular the sensor can comprise a camera and/or an optical marker and/or a medical imaging system and/or a motion sensor and/or an electrocardiogram electrode etc.

Connected can mean in this context that the detection apparatus is integrated into the control apparatus. In particular the detection apparatus can comprise a C-arm for example. Then the sensor comprises an imaging system of the C-arm. In particular the C-arm can then be integrated into the control apparatus. In particular the control apparatus and the detection apparatus integrated into the control apparatus can exchange data.

As an alternative the detection apparatus can be connected to the control apparatus in such a way that the two apparatuses can exchange data, wherein they are physically separated. In particular the detection apparatus can transmit information about the current movement state of the examination object to the control apparatus over the connection. In particular the control apparatus can receive the information or data from the detection apparatus. In particular the apparatuses can be electrically connected. In particular the apparatuses can be connected via cables.

At least one embodiment of the invention also relates to a display apparatus for output of the control signal.

In particular the display apparatus is embodied to output the control signal for a medical professional. In particular the control signal can be provided via the display apparatus.

In particular the display apparatus can comprise a screen. In particular the screen can be embodied to display text and/or pictures. In particular the display apparatus can be embodied to display the control signal in the form of text or pictures. In particular the screen can be a tube screen or an LED screen or a plasma screen etc.

In particular the display apparatus can be connected to a control apparatus. In particular the display apparatus can be connected to the control apparatus in such a way that the control signal, which is provided by the control apparatus, is received by the display apparatus. In particular the control apparatus and the display apparatus can be connected electrically. In particular the control apparatus and the display apparatus can be connected via cables.

As an alternative the display apparatus can be integrated into the control apparatus. In other words the control apparatus can feature the display apparatus.

At least one embodiment of the invention also relates to a computer program product with a computer program as well as to a computer-readable medium. A largely software-based realization has the advantage that the control apparatus already used can easily be upgraded by a software update in order to work in the way described. Such a computer program product, as well as the computer program, can if necessary comprise further elements such as e.g. documentation and/or additional components, as well as hardware components, such as e.g. hardware keys (dongles etc.) for use of the software.

In particular, at least one embodiment of the invention also relates to a computer program product with a computer program, which is able to be loaded directly into a memory of a control apparatus, with program sections for carrying out all steps of the method of at least one embodiment, for creating a control signal for controlling a movement of a medical object described above when the program sections are executed by the control apparatus.

In particular, at least one embodiment of the invention relates to a computer-readable storage medium, on which program sections able to be read and executed by a determination system and/or a training system are stored, in order to carry out all steps of at least one embodiment of the method described above for creation of a control signal for controlling a movement of a medical object when the program sections are executed by the control apparatus.

FIG. 1 shows a flow diagram of a first example of an example embodiment of the method for creation of a control signal for controlling a movement of a medical object MO.

In the method step of receipt REC-1 of a first medical image dataset at least one medical image is received. In particular the first medical image dataset can comprise a chronological series of medical images. In particular the first medical image dataset can have been acquired with a computed tomography device, a C-arm, a magnetic resonance tomography device, a 3D ultrasound etc. In the first medical image dataset at least one movement state MS of at least one part of the examination object 31 is detected. In particular a chronological series of movement states MS of the part of the examination object 31 can be detected in the first medical image dataset. The part of the examination object 31 comprises an organ in which the medical object MO is to be moved. The organ comprises a vascular system VS with vascular sections VSec and vascular branches VB, along which the medical object MO is to be moved.

A movement state MS can depend for example on a support or position of the examination object 31 and/or on a heart movement or a heart state and/or on a breathing movement or a breathing state and/or on a movement of the digestive system etc.

In the method step of determination DET-1 of a movement model, the movement model is determined based on the first medical image dataset. The movement model for the at least one part of the examination object 31 is determined. The movement model comprises at least the movement states MS or the movement state MS, which is detected in the first medical image dataset. By way of biomechanical modeling further movement states MS are modeled in the movement model. For the biomechanical modeling movement states MS are modeled with reference to known material properties of the part of the examination object 31 acquired in the first medical image dataset. In this case material properties such as rigidity, interaction with surrounding tissue etc. are taken into account. Moreover the support or position of the examination object 31 is taken into account in the biomechanical modeling of movement states MS. In particular the movement model then comprises at least one target movement state.

In the target movement state the medical object MO can be moved or guided as easily as possible along a desired movement path MP to a target position TP. The target movement state can also comprise a chronological series of movement states MS. The target movement state can be determined manually. As an alternative the target movement state can be determined automatically with the aid of the movement model.

In the method step of detection REC-2 of the current movement state of the examination object 31 the current movement state is detected with a sensor. The current movement state is the movement state MS of the examination object 31, which the examination object 31 assumes at a current point in time. The sensor can comprise a number of components. For example the sensor can comprise a camera 52 with or without optical markers 51. The optical marker 51 can be arranged for example in the chest and/or stomach area of the examination object 31. The movement of the optical marker 51 can be recorded and evaluated with the camera 52. From the movement conclusions can be drawn about the current movement state. In particular a breathing movement or a breathing state of the examination object 31 can be detected in this way. As an alternative the camera 52 can detect the movement of the examination object 31 without optical markers 51. By way of image processing conclusions can likewise be drawn from this recording as to the current movement state. As an alternative or in addition the sensor can comprise an EKG system. From an EKG signal of the EKG system the current movement state, in particular the heart movement of the examination object 31 can be derived. As an alternative or in addition the sensor can comprise a breathing device for example. By way of the breathing device the breathing state of the examination object 31 can be set and from this the current movement state can be derived. As an alternative or in addition the sensor can comprise a medical imaging system. The medical imaging system can for example be a C-arm 37 or a 3D ultrasound device or a CT device or a magnetic resonance tomography device or a flat panel x-ray device, etc.

In the method step of comparing DET-2 whether the current movement state of the examination object 31 at least approximately corresponds to the target movement state, a trigger signal is output for example, which specifies that the target movement state corresponds to the current movement state. This initiates the following method step. For comparing the movement states the sensor signal detected in the method step of detection REC-2 of the current movement state can be compared with a comparison sensor signal. In this case at least the target movement state is linked in the movement model to a comparison sensor signal. The comparison sensor signal has been detected with a sensor, which is equivalent to the sensor for detection REC-2 of the current movement state. In this way the two sensor signals can be compared. As an alternative a number of movement states can be linked in the movement model to a comparison sensor signal. As an alternative each movement state in the movement model can be linked to a comparison sensor signal.

The next method step can be the determination DET-3 of the control signal. As an alternative this method step can be carried out directly after the method step of determination DET-1 of the movement model. The control signal is determined based on the movement model and the current movement state. In this case the current movement state corresponds at least approximately to the target movement state. As an alternative a control signal can have been determined beforehand for a number of movement states in the movement model. In this case, in the method step of determination DET-3 of the control signal, the control signal is "sought out" which belongs to the target movement state, which at least approximately corresponds to the current movement state. The control signal describes the movement that the medical object MO must make so that it can be moved or guided in the target movement state through the vascular system VS to the target position TP. The control signal describes the spatial direction and the orientation of the medical object MO for the movement. The control signal for example describes a rotation of the medical object MO about its own axis. As an alternative or in addition the control signal can describe a bending of the medical object MO about an axis. In this case the control signal can moreover describe a spatial direction and a radius of this bending. Moreover the control signal can describe when the target movement state at least approximately corresponds to the current movement state. For this the control signal can comprise a likely or predicted point in time for this. This point in time can be determined by extrapolation of a chronological series of sensor signals from the step of detecting the current movement state.

In the method step of provision PROV-1 the control signal for movement of the medical object MO is provided.

The control signal can in particular be provided via a display apparatus 42. This can display the control signal in text or pictorial form to a medical professional when the medical professional is to move the medical object MO.

As an alternative the control signal can be provided to a robot R which moves the medical object MO.

In example embodiments the control signal can only be output when the medical object MO gets closer than a predefined distance from a critical point CP. The critical point CP can be defined manually or automatically. The critical point CP can for example be a point with a high degree of branches. As an alternative or in addition a vessel diameter of the vessel section VSec at the critical point CP can be comparatively small. As an alternative or in addition a form of the critical point CP can be heavily dependent on the movement state MS of the examination object 31. In other words the critical point CP can move and/or deform markedly with the movement of the examination object 31.

Figure 2:
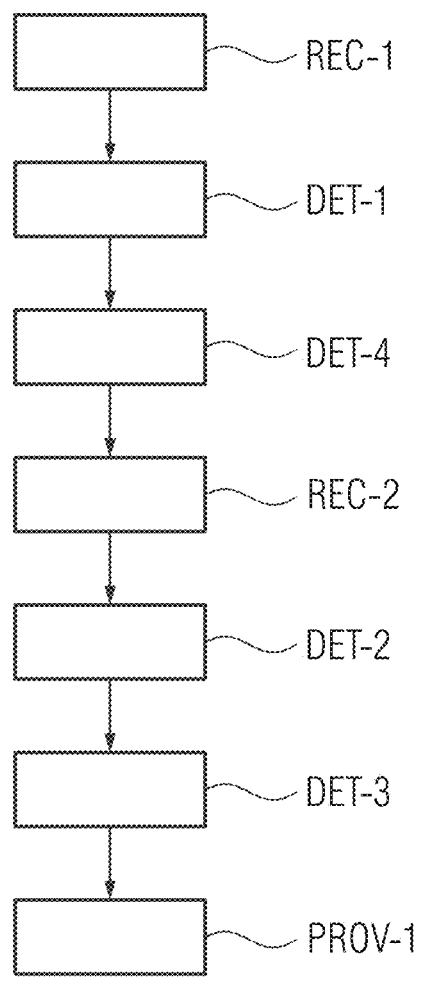
FIG. 2 shows a flow diagram of a second example of an example embodiment of the method for creation of a control signal for controlling a movement of a medical object.

FIG. 2 shows a flow diagram of a second example embodiment of the method for creation of a control signal for controlling a movement of a medical object MO.

The method steps of receipt REC-1 of a first medical dataset, of determination DET-1 of a movement model, of detection REC-2 of a current movement state, of comparing DET-2 whether the current movement state at least approximately corresponds to a target movement state, of determination DET-3 of the control signal and of provision PROV-1 of the control signal are carried out in a similar way to that given in the description in accordance with FIG. 1.

In this example embodiment, after the determination DET-1 of the movement model, the method step of the determination DET-4 of a movement path MP based on the movement model is carried out. The movement path MP describes in particular the spatial direction of a movement of a medical object MO. The movement path MP describes a path from a current position or a start position SP of the medical object MO in the vascular system VS to a target position TP. The movement path MP can be determined for example by solving a minimization problem. Initially the vascular system VS can be segmented in the movement states MS of the movement model and by way of a skeletonization algorithm a center line of the vascular system VS can be determined. The movement states MS in the movement model can be present for this in the form of medical images. As an alternative the steps of the segmentation and of the application of the skeletonization algorithm can already have been carried out in the determination of the movement model. Along this center line different paths can be determined from the start position SP to the target position TP. The shortest of these paths can be the movement path MP. As an alternative the movement path MP can be the path that runs through the vascular sections VSec with a greatest vessel diameter.

As an alternative the movement path MP can be determined by way of machine learning.

As an alternative the movement path MP can be determined manually by a medical professional.

The movement path MP can be determined for all movement states MS in the movement model. To save computing time the movement path MP can be determined for just the target movement state of the movement model when the target movement state is known.

The target movement state can be defined manually, for example by the medical professional. As an alternative the target movement state can be determined based on the movement path MP. Movement paths MP of different movement states MS in the movement model can be compared for this. In particular the movement state MS can be defined as the target movement state, in which for example the vessel diameter of the vessel section VSec in which the medical object MO is to be moved is of maximum size. As an alternative or in addition the movement state MS can be defined as the target movement state in which a vessel branch VB through which the medical object MO is to be moved is aligned in such a way that a movement in the corresponding vessel section VB is as easy as possible to carry out.

In alternative example embodiments the method step of determination DET-4 of the movement path MP can be carried out at any point after the determination DET-1 of the movement model and before the determination DET-3 of the control signal.

Figure 3:
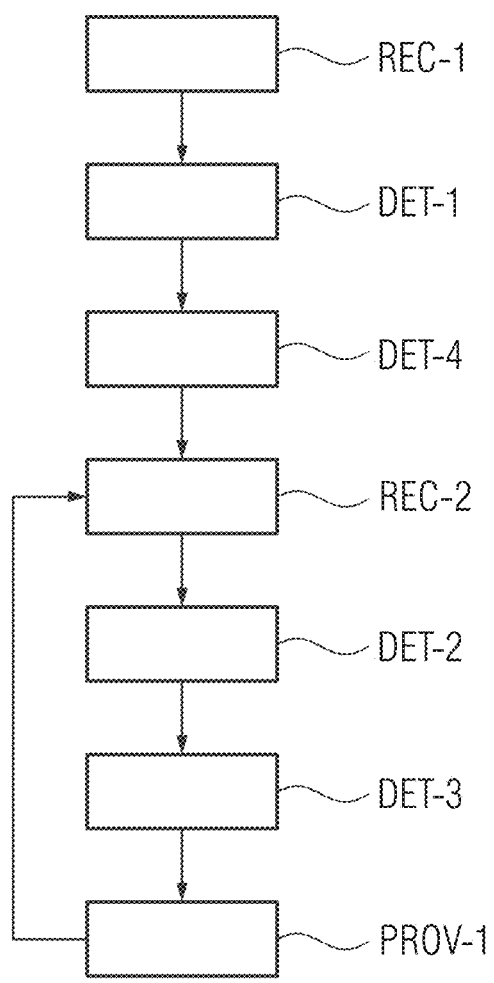
FIG. 3 shows a flow diagram of a third example of an example embodiment of the method for creation of a control signal for controlling a movement of a medical object.

FIG. 3 shows a flow diagram of a third example embodiment of the method for creation of a control signal for controlling a movement of a medical object MO.

The method steps of the example embodiment shown are carried out as described in accordance with FIGS. 1 and 2. In this example embodiment a loop is executed via the method steps of detection REC-2 of a current movement state, of comparing DET-2 whether the current movement state at least approximately corresponds to a target movement state, of determination DET-3 of the control signal and of provision PROV-1 of the control signal. The loop can comprise at least one execution of the loop. In particular the loop can comprise as many executions of the loop as would enable the medical object MO to be moved with the aid of the control signals to the target position TP.

In particular, depending on a current position of the medical object MO in a vascular system VS, a control signal can be provided. In other words the control signal that is provided during the executions of the loop can be different. In particular the loop can be executed for a multiplicity of critical points CP.

Figure 4:
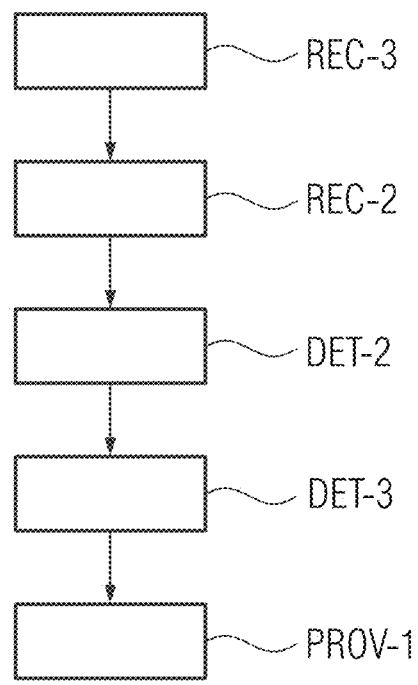
FIG. 4 shows a flow diagram of a fourth example of an example embodiment of the method for creation of a control signal for controlling a movement of a medical object.

FIG. 4 shows a flow diagram of a fourth example embodiment of the method for creation of a control signal for controlling a movement of a medical object MO.

The method steps of detection REC-2 of a current movement state, of comparing DET-2 whether the current movement state at least approximately corresponds to a target movement state, of determination DET-3 of the control signal and of provision PROV-1 of the control signal are carried out in a similar way to the description given in accordance with FIG. 1.

As an alternative to the method steps of receipt REC-1 of a first medical image dataset and of determination DET-1 of a movement model in accordance with FIG. 1, in this example embodiment the movement model is received in a method step of receipt REC-3 of the movement model. The movement model is embodied in this case in a similar way to that described in accordance with FIG. 1.

The example embodiments in accordance with FIGS. 2 and 3 can also be carried out in a similar way for this example embodiment.

Figure 5:
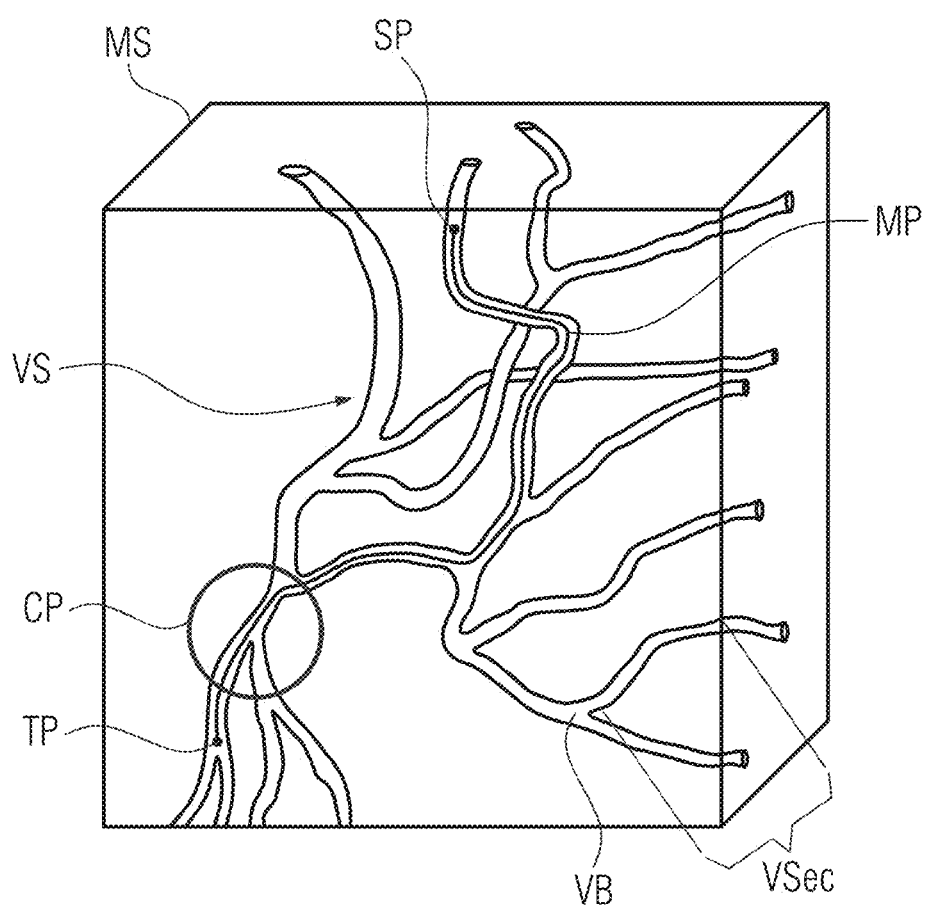
FIG. 5 shows a schematic diagram of a vascular system for a movement state with a movement path.

FIG. 5 shows a schematic diagram of a vascular system VS for a movement state MS with a movement path MP.

The vascular system VS is shown in a movement state MS. The movement state MS is encompassed by the movement model. The movement state MS can be represented in the form of a three-dimensional medical image. In particular the vascular system VS is then shown as a three-dimensional medical image. A vessel section VSec and a vessel branch VB are marked by way of example in the diagram.

In the movement state MS a movement path MP is depicted. The movement path MP runs from a start position SP to a target position TP. The medical object MO can be moved along the movement path MP in order to be moved from the start position SP to the target position TP.

For example a critical point CP is marked with a circle in the diagram. At the critical point CP the movement path MP leads through a vessel branch VB. In different movement states MS there can be different degrees of complexity in striking the correct vessel branch VB with the medical object MO. In the diagram shown a number of critical points CP can be defined. For the sake of clarity just one critical point CP is depicted.

With the aid of the movement path MP control signals can be output. The control signals can describe the direction in which the medical object MO is to be moved. Moreover the control signals can specify whether the medical object MO is to be rotated about its own axis and/or whether the axis of the medical object MO is to be bent.

Figure 6:
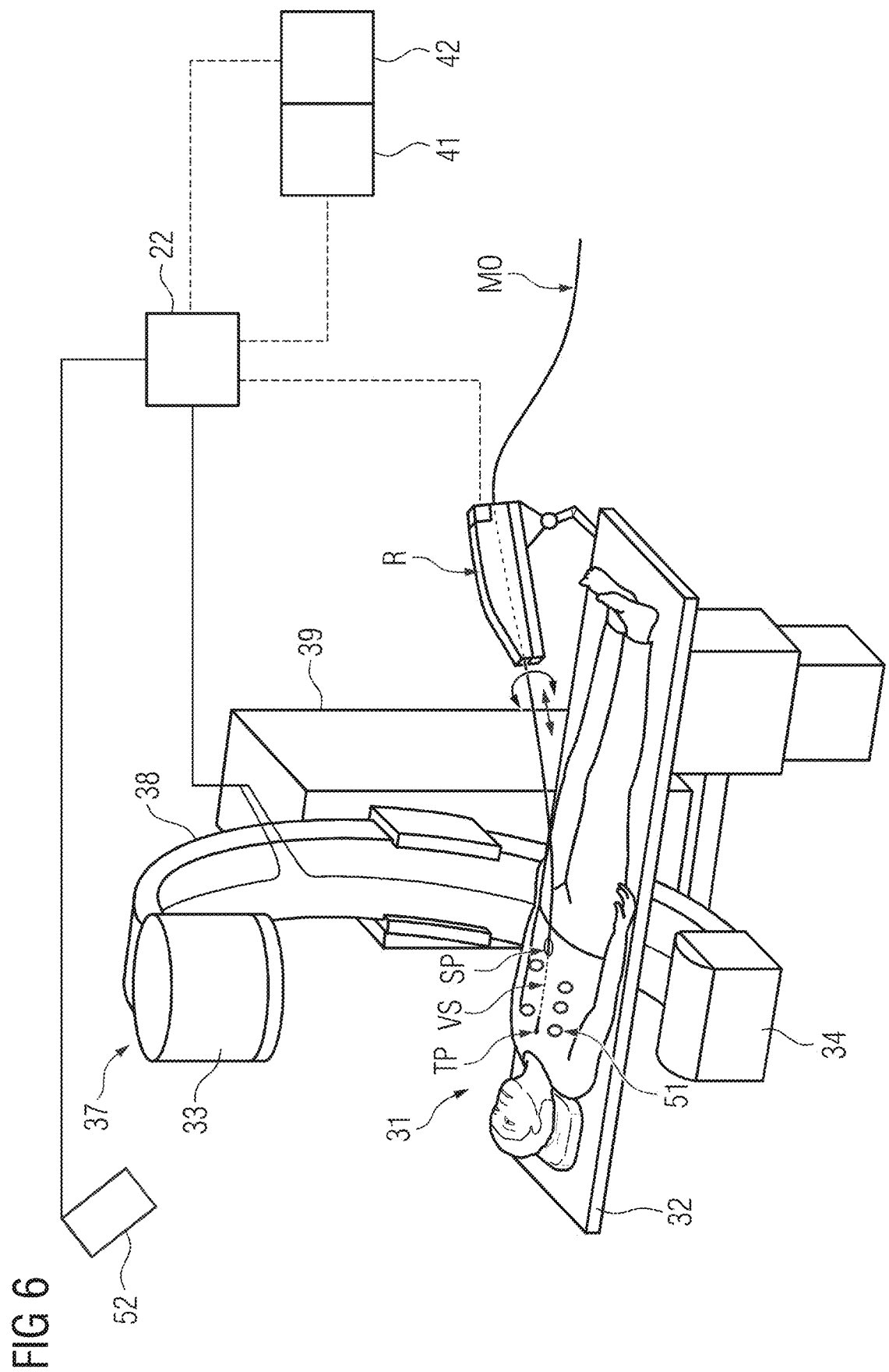
FIG. 6 shows a schematic diagram of a control apparatus with a detection apparatus and a display apparatus.

FIG. 6 shows a schematic diagram of a control apparatus 22 with a C-arm 37 and a camera 52 with optical markers 51 as detection apparatus and a display apparatus 42.

In the example embodiment shown the examination object 31 can be supported or positioned on a couch 32. In particular the examination object 31 can be a patient who is positioned on a patient couch. As an alternative the examination object 31 can be a human dummy which can be used for simulation of the method described.

In this example embodiment a medical object MO is introduced into the examination object 31. The medical object MO can be a catheter or an endoscope for example. The medical object MO is to be moved along a vascular system VS not discernable in the diagram from a start position SP to a target position TP.

The detection apparatus in this example embodiment comprises a C-arm 37 and a combination of a camera 52 and optical markers 51. In particular the sensor comprises an image sensor of the C-arm 37 and the camera 52. With the detection apparatus a sensor signal is detected. The sensor signal serves to determine the current movement state.

The C-arm 37 comprises an x-ray source 33 and an x-ray detector 34. The x-ray source 33 and the x-ray detector 34 are arranged lying opposite one another on a C-arm 38. They are arranged in such a way that radiation emitted by the x-ray source 33 penetrates the examination object 31 so that a medical image of the vascular system VS with the start position SP and the target position TP can be recorded with the x-ray detector 34. This medical image represents the current movement state of the examination object 31 at the point in time of the recording. The medical image is forwarded to the control apparatus 22.

The detection apparatus moreover comprises the camera 52 which is embodied to detect a movement of the optical markers 51. In the diagram, for the sake of clarity, just one optical marker 51 is labeled with the reference character. All circular markings on the chest of the examination object 31 not otherwise identified are likewise optical markers 51. From the movement of the optical markers 51 the current movement state of the examination object 31 can be deduced. In particular the current movement state of the breathing can be deduced. The information about the current movement state that is detected with the camera 52 is likewise forwarded to the control apparatus 22.

In alternative example embodiments the detection apparatus can comprise further components such as for example an EKG device, a respirator device, etc.

Furthermore a medical professional can transfer further information to the control apparatus 22 by entering it via an input unit 41. In order to illustrate that this input is an option, the connection between the input unit 41 and the control apparatus 22 is depicted as a dashed line. The medical professional can mark critical points CP via the input unit 41 for example, mark distances to the critical points CP from which a control signal is to be output, draw in a movement path MP in a movement model, define target movement states, etc.

The control apparatus 22 has already received a first medical image dataset in advance and modeled a movement model from it. Moreover a movement path MP has been determined, along which the medical object MO is to be moved from the start position SP to the target position TP. The movement path MP has been determined for a target movement state or for a chronological series of target movement states or for a multiplicity of target movement states. Depending on a current position of the medical object MO on the movement path MP, the target movement state can be different. As an alternative the movement path MP and/or the target movement state can be determined by a medical expert via the input unit 41.

The control apparatus 22 can compare, with the aid of the data from the camera 52 and the C-arm 37, whether the current movement state at least approximately corresponds to the target movement state according to the current position of the medical object MO. When the two movement states MS at least approximately correspond to one another, the control apparatus 22 can output a control signal. The control signal describes the movement that the medical object MO must carry out in order to follow the movement path MP further. The control signal can be embodied as above, in particular as described in accordance with FIG. 1.

In alternative versions the control apparatus can already output the control signal before the current movement state at least approximately corresponds to the target movement state. In this case the control signal also describes when the current movement state at least approximately corresponds to the target movement state. The likely or predicted point in time for the correspondence of the two movement states can be displayed via the display apparatus. For this the display apparatus can for example display a countdown until the occurrence of the predicted time of the at least approximate correspondence between the two movement states.

The control signal can be provided to a display apparatus 42. The display apparatus 42 can show the control signal to the medical professional in a form in which the medical professional can employ the control signal as assistance for carrying out the movement of the medical object MO. For example the display apparatus 42 can show the control signal in the form of text or pictures. For example the displayed text can describe how and in which spatial direction the medical object MO is to be moved. As an alternative or in addition the type and the spatial direction of the movement of the medical object MO can be shown in an image. For example the control signal can be shown as a pictogram. As an alternative the control signal can be shown superimposed on the current medical image that is recorded by the C-arm 37. In particular the control signal can be depicted with arrows in the medical image. Moreover the control signal can be shown when the current movement state corresponds to the target movement state. As an alternative the control signal can be shown briefly in advance before the current movement state corresponds to the target movement state so that the medical professional has enough reaction time to carry out the movement. In particular the predicted point in time of the occurrence of the target movement state can then additionally be shown. The point in time of the display can be determined by way of the movement model. The connection between the control apparatus 22 and the display apparatus 42 is shown as a dashed line in the diagram since the connection is optional.

As an alternative the control signal can be provided to a robot R which carries out the movement of the medical object MO as described by the control signal. This connection is depicted in the diagram as a dashed line since the connection is optional. The carrying out of the movement is in particular not an element of the invention.

In alternative example embodiments the control apparatus 22 can determine the measures by which the current movement state is to be translated into the target movement state. In particular the control apparatus 22 can provide information about this to the display apparatus 42. In particular the display apparatus 42 can display to the medical professional in text and/or in pictorial form a process by which the target movement state can be established. In particular the process can be described by text. As an alternative the process can be shown with the aid of pictograms. As an alternative or in addition the control apparatus 22 can pass on or provide the information to a respirator unit. The respirator unit can explicitly control a breath frequency, a breath amplitude and/or breath pauses in such a way that the examination object 31 assumes the target movement state.

Figure 7:
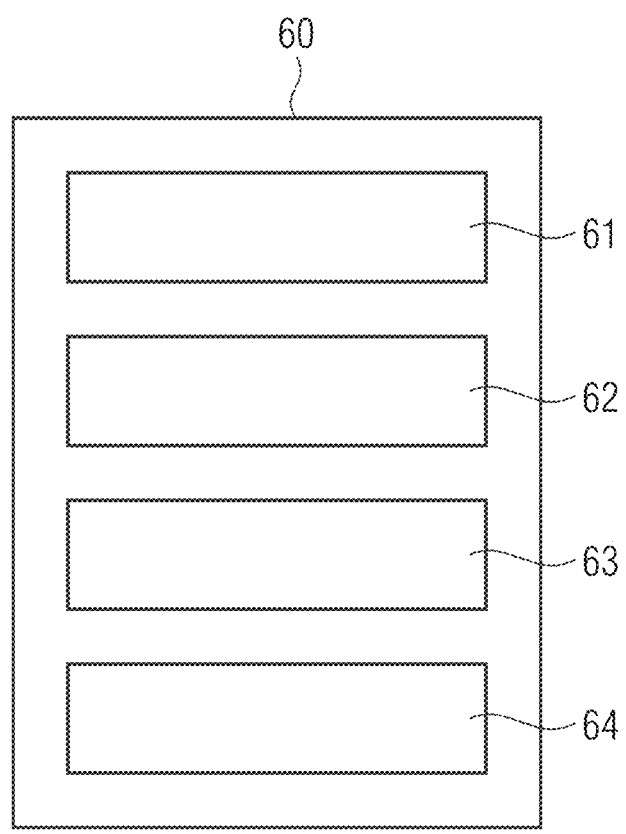
FIG. 7 shows a control apparatus.

FIG. 7 shows a control apparatus 60 for creation of a control signal for controlling a movement of a medical object MO. The control apparatus 60 shown here is designed to carry out an inventive method. This control apparatus 60 comprises an interface 61, a processor 62, a memory unit 63 and also an input and output unit 64. In this case the input unit 41 in accordance with FIG. 5 can be an element of the input and output unit 64. In this case the interface 61 can in particular comprise further interfaces or sub-interfaces. Furthermore the processor 62 can in particular comprise further processors or sub-processors.

The control apparatus 60 can in particular involve a computer, a microcontroller or an integrated circuit. As an alternative the control apparatus 60 can involve a real or virtual network of computers (known as a cluster or a cloud respectively).

An interface 61 can involve a hardware or software interface (for example PCI bus, USB or Firewire). A processor 62 can have hardware elements or software elements, for example a microprocessor or so-called FPGA (Field Programmable Gate Array). A memory unit 63 can be realized as non-permanent working memory (Random Access Memory, abbreviated as RAM) or as permanent mass storage (hard disk, USB stick, SD card, Solid State Disk). An input and output unit 64 comprises at least one input unit 42 and/or at least one output unit.

An input unit 42 can be realized in particular by way of a keyboard and/or a mouse. An output unit can in particular involve a screen. As an alternative it can also involve a printer that is embodied to print out pictorial data.

Where not explicitly the case, but sensible and in the spirit of the invention however, individual example embodiments, individual elements of their sub-aspects or features can be combined with each other, without departing from the framework of this invention. Advantages of the invention described with regard to one example embodiment, where transferrable, also apply, without this being explicitly stated, to other example embodiments.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for creation of a control signal with regard to controlling a movement of a medical object, the creation of the control signal being dependent on a current movement state of an examination object, the computer-implemented method comprising:
   receiving, via a processor, a movement model of at least one part of the examination object, the movement model including at least one target movement state of the examination object;
   detecting, via a sensor, a current movement state of the examination object;
   comparing, via the processor, the current movement state and the at least one target movement state;
   determining, via the processor, the control signal as a function of the movement model and of the current movement state, depending on a result of the comparing; and
   provisioning the control signal,
   wherein the control signal describes a direction and orientation of movement of the medical object and triggers the movement of the medical object and the control signal is only provided when the medical object is at less than a threshold distance from a critical point, the critical point and the threshold distance being derived from the movement model.

2. The method of claim 1, wherein at least the one target movement state of the movement model is linked to a comparison sensor signal.

3. The method of claim 1, further comprising:
   determining a movement path, the movement path describing a spatial direction of the movement of the medical object, the determining of the movement path being based on the movement model.

4. The method of claim 3, wherein the determining of the movement path for the target movement state takes place in the movement model.

5. The method of claim 1, wherein the current movement state is detected by at least one of detecting a breathing state, detecting an EKG signal, detecting via optical tracking of the examination object and detecting a current medical image dataset.

6. The method of claim 1, wherein the target movement state is brought about by at least one of
   support of the examination object determined from the movement model,
   exertion of a specific force on the examination object, with aid of a display apparatus,
   with aid of specifications with regard to breathing for the examination object, and
   a respirator unit.

7. The method of claim 1, wherein the control signal describes when the target movement state at least approximately corresponds to the current movement state.

8. The method of claim 1, wherein the control signal is output to a display apparatus.

9. The method of claim 1, wherein the detecting, comparing, determining and provisioning are carried out in a loop.

10. The method of claim 1, wherein the control signal is determined as a function of the movement model and of the current movement state in response to the target movement state at least approximately corresponding to the current movement state.

11. A computer-implemented method for creation of a control signal with regard to controlling a movement of a medical object, the creation of the control signal being dependent on a current movement state of an examination object, the computer-implemented method comprising:
    receiving, via a processor, a first medical image dataset, the first medical image dataset representing at least one part of the examination object;
    determining, via the processor, a movement model of the at least one part of the examination object based on the first medical image dataset, the movement model including at least one target movement state of the examination object;
    detecting, via a sensor, a current movement state of the examination object;
    comparing, via the processor, the current movement state and the at least one target movement state;
    determining, via the processor, the control signal as a function of the movement model and of the current movement state, depending on a result of the comparing; and
    provisioning the control signal,
    wherein the control signal describes a direction and orientation of movement of the medical object and triggers the movement of the medical object and the control signal is only provided when the medical object is at less than a threshold distance from a critical point, the critical point and the threshold distance being derived from the movement model.

12. The method of claim 11, further comprising:
    determining a movement path, the movement path describing a spatial direction of the movement of the medical object, the determining of the movement path being based on the movement model.

13. The method of claim 12, wherein the determining of the movement path for the target movement state takes place in the movement model.

14. The method of claim 11, wherein the control signal is output to a display apparatus.

15. The method of claim 11, wherein the detecting, comparing, determining of the control signal and provisioning are carried out in a loop.

16. A control apparatus for creation of a control signal, with regard to controlling a movement of a medical object, dependent on a current movement state of an examination object, the control apparatus comprising:
- a processor, configured to receive a movement model of at least one part of the examination object, the movement model including at least one target movement state of the examination object, the processor being further configured to
- compare the current movement state and the target movement state;
- determine the control signal as a function of the movement model and of the current movement state; and
- provide the control signal,
  - wherein the control signal describes a direction and orientation of movement of the medical object and triggers the movement of the medical object and the control signal is only provided when the medical object is at less than a threshold distance from a critical point, the critical point and the threshold distance being derived from the movement model.

17. A detection apparatus, connected to the control apparatus of claim 16, for transmission of information with regard to a current movement state, comprising:
- a sensor, embodied to detect the current movement state.

18. A display apparatus, for output of the control signal of the control apparatus of claim 16.

19. A non-transitory computer-readable storage medium, storing readable and executable program sections, to carry out the method of claim 1 when the executable program sections are executed by a control apparatus.

20. A non-transitory computer-readable storage medium, storing readable and executable program sections, to carry out the method of claim 11 when the executable program sections are executed by a control apparatus.

* * * * *